United States Patent
Kwon et al.

(10) Patent No.: US 9,259,395 B2
(45) Date of Patent: Feb. 16, 2016

(54) TUMOR-TARGETING GAS-GENERATING NANOPARTICLE, METHOD FOR PREPARING THE SAME, AND TUMOR-TARGETING NANOPARTICLE FOR DRUG DELIVERY USING THE SAME

(71) Applicant: KOREA INSTITUTE OF SCIENCE AND TECHNOLOGY, Seoul (KR)

(72) Inventors: Ick Chan Kwon, Seoul (KR); Kwang Meyung Kim, Seoul (KR); Kuiwon Choi, Seoul (KR); Heebeom Koo, Seoul (KR); Hyun Su Min, Daejeon (KR); Inchan Youn, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 81 days.

(21) Appl. No.: 13/906,963

(22) Filed: May 31, 2013

(65) Prior Publication Data
US 2013/0323177 A1 Dec. 5, 2013

(30) Foreign Application Priority Data
May 31, 2012 (KR) .................. 10-2012-0058600

(51) Int. Cl.
| | | |
|---|---|---|
| A61B 8/00 | (2006.01) |
| A61K 9/51 | (2006.01) |
| A61K 49/22 | (2006.01) |
| A61K 41/00 | (2006.01) |
| A61K 47/48 | (2006.01) |
| A61K 49/00 | (2006.01) |
| A61K 9/00 | (2006.01) |

(52) U.S. Cl.
CPC ............ *A61K 9/5146* (2013.01); *A61K 9/0009* (2013.01); *A61K 9/0019* (2013.01); *A61K 9/5153* (2013.01); *A61K 41/0028* (2013.01); *A61K 47/48869* (2013.01); *A61K 49/0032* (2013.01); *A61K 49/0054* (2013.01); *A61K 49/0093* (2013.01); *A61K 49/222* (2013.01); *A61K 49/225* (2013.01); *A61K 9/0004* (2013.01)

(58) Field of Classification Search
USPC ........................................................ 424/9.5
See application file for complete search history.

(56) References Cited

U.S. PATENT DOCUMENTS

| | | | |
|---|---|---|---|
| 2012/0121718 A1* | 5/2012 | Lai et al. ................ | 424/497 |
| 2012/0321719 A1* | 12/2012 | McDonnell et al. ......... | 424/497 |

FOREIGN PATENT DOCUMENTS

KR    10-1127895    3/2012

OTHER PUBLICATIONS

Nanowerk (Nanomedicine: Loading up a cure http://www.nanowerk.com/news/newsid=21311.php).*
Kang et al. (Angew. Chem. Int. Ed. 2010, 49, 524-528).*
Bazile et al. (J. Pharm. Sci. 1995, 84, 493-498).*

* cited by examiner

*Primary Examiner* — Michael G Hartley
*Assistant Examiner* — Melissa Perreira
(74) *Attorney, Agent, or Firm* — Goldilocks Zone IP Law

(57) ABSTRACT

A tumor-targeting gas-generating nanoparticle, a method for preparing same and a tumor-targeting nanoparticle for drug delivery using same relate to a tumor-targeting gas-generating nanoparticle including a polycarbonate core and a amphiphilic coat, a method for preparing same and a tumor-targeting nanoparticle for drug delivery using same. Since a tumor-targeting gas-generating nanoparticle according to the present disclosure is accumulated in the tumor tissue in large quantity and generates strong ultrasound wave signals, it can be usefully used as a contrast agent for ultrasonic imaging.

7 Claims, 11 Drawing Sheets

TUMOR-TARGETING GAS-GENERATING NANOPARTICLE, METHOD FOR PREPARING THE SAME, AND TUMOR-TARGETING NANOPARTICLE FOR DRUG DELIVERY USING THE SAME

CROSS-REFERENCE TO RELATED APPLICATIONS

This application claims priority under 35 U.S.C. §119 to Korean Patent Application No. 10-2012-0058600 filed on May 31, 2012, in the Korean Intellectual Property Office, the disclosure of which is incorporated herein by reference in its entirety.

TECHNICAL FIELD

The present disclosure relates to a gas-generating nanoparticle which is specifically accumulated in a tumor and generates a gas and a nanoparticle for drug delivery using same.

BACKGROUND

At present, ultrasonic imaging is an imaging technique the most frequently used for clinical diagnosis. It is attracting a lot of attentions owing to many advantages including low cost, easiness of diagnosis, non-invasiveness, low risk and possibility of direct real-time imaging. Basically, ultrasonic imaging is based on the analysis of sound wave signals obtained by reflecting or scattering high-frequency sound from tissues. Various contrast agents for ultrasonic imaging have been developed to obtain more improved images and they are used for diverse biomedical purposes.

Most of the contrast agents for ultrasonic imaging are substances that generate microbubbles. The microbubble contrast agent consists of a gas included therein and an outer coat material. The microbubbles vibrate at the sound wavelength to generate enhanced ultrasound wave signals as compared to the surrounding region. However, they are not suitable for wide applications owing to very short circulation time of about several minutes and poor tissue permeation. These shortcomings result from the micro size of the contrast agents for ultrasonic imaging, which is too large to pass through the many biological barriers existing in organs and capillary vessels.

Recently, nanoparticles have emerged as a promising platform for biomedical imaging and drug delivery. Nanoparticles can circulate in the bloodstream stably for a long time and can be accumulated in angiogenic disease sites such as tumors by penetrating the newly formed blood vessels. This phenomenon, called the enhanced permeation and retention (EPR) effect, is the main advantage of nanomaterials for tumor targeting, particularly in intravenous injection. The target-specific accumulation of nanoparticles is useful both in imaging and drug delivery. Especially, multifunctional nanoparticles allow diagnosis and therapy at the same time, and this is called 'theragnosis'. Although theragnosis is expected to provide more improved therapy clinically, nanobubbles are hardly used in ultrasonic imaging since they fail to generate ultrasound wave signals of sufficient intensity unlike the microbubbles even when the composition is similar. That is to say, although the nano size is favorable in terms of long-term circulation and accumulation in target tissues, it is disadvantageous in terms of generation of ultrasound wave signals. This is an important dilemma in the development of contrast agents for ultrasonic imaging.

In this regard, the inventors of the present disclosure have recently a new type of contrast agent for ultrasonic imaging based on a polycarbonate that generates a gas. This contrast agent is degraded in an aqueous condition to generate carbon dioxide bubbles. The generated bubbles can successfully generate ultrasound wave signals at sound wavelength like the commercially available microbubble-type contrast agents for ultrasonic imaging. The particles exhibit continuous generation of gas, thus enabling stable ultrasonic imaging for a long time. In addition, the inventors of the present disclosure have demonstrated that the amount and duration of generated carbon dioxide gas are mainly determined by contact with water and they can be adequately controlled through structural modification of particles (see Korean Patent Application No. 2009-100417).

SUMMARY

The present disclosure is directed to providing a tumor-targeting gas-generating nanoparticle having enhanced circulation time and tissue permeation effect and capable of generating ultrasound wave signals of stronger intensity as compared to the existing contrast agent for ultrasonic imaging, a method for preparing same and a tumor-targeting nanoparticle for drug delivery using same.

In one general aspect, there is provided a tumor-targeting gas-generating nanoparticle including a polycarbonate core and an amphiphilic coat.

In an exemplary embodiment of the present disclosure, the polycarbonate core may be poly(cholesteryl γ-butyrolactone-b-propylene oxide) represented by Chemical Formula 1:

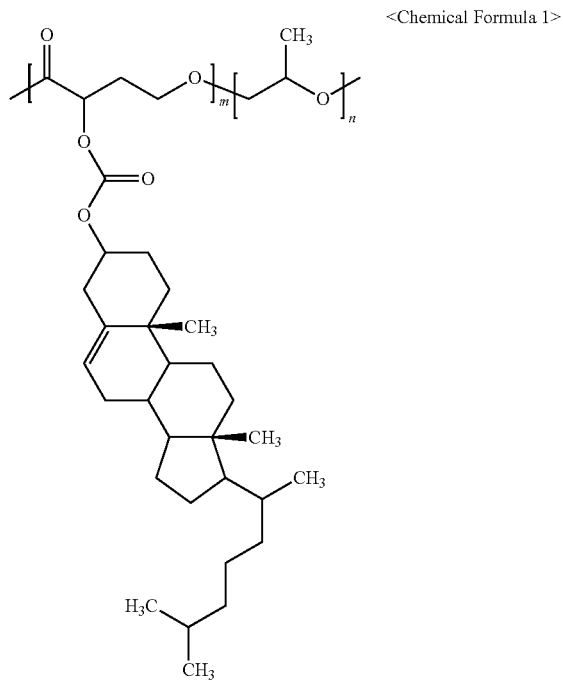

<Chemical Formula 1> wherein each of m and n is an integer from 1 to 1000.

In another exemplary embodiment of the present disclosure, the amphiphilic coat may be a polyethylene oxide-polypropylene oxide-polyethylene oxide triblock copolymer, a polyethylene oxide-polyglycoliclactic acid copolymer or a polyethylene oxide-polylactic acid copolymer.

In another exemplary embodiment of the present disclosure, the nanoparticle may have a particle size distribution of 300±50 nm.

In another general aspect, there is provided a method for preparing a tumor-targeting gas-generating nanoparticle, including:

synthesizing a polycarbonate core through ring-opening polymerization; and encapsulating the polycarbonate core with an amphiphilic coat through oil-in-water emulsification.

In an exemplary embodiment of the present disclosure, the polycarbonate core may be poly(cholesteryl γ-butyrolactone-b-propylene oxide) represented by Chemical Formula 1:

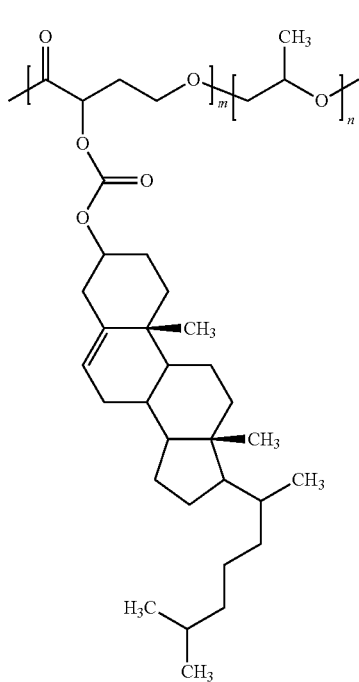

<Chemical Formula 1> wherein each of m and n is an integer from 1 to 1000.

In another exemplary embodiment of the present disclosure, the amphiphilic coat may be a polyethylene oxide-polypropylene oxide-polyethylene oxide triblock copolymer, a polyethylene oxide-polyglycoliclactic acid copolymer or a polyethylene oxide-polylactic acid copolymer.

In another general aspect, there is provided a tumor-targeting nanoparticle for drug delivery including:

a core comprising a drug to be delivered and a polycarbonate; and an amphiphilic coat.

In an exemplary embodiment of the present disclosure, the polycarbonate core may be poly(cholesteryl γ-butyrolactone-b-propylene oxide) represented by Chemical Formula 1:

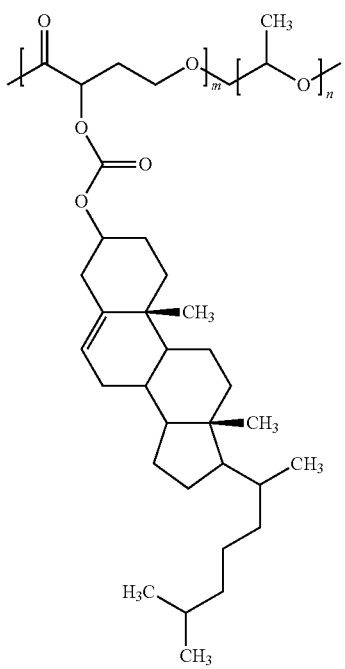

<Chemical Formula 1> wherein each of m and n is an integer from 1 to 1000.

In another exemplary embodiment of the present disclosure, the amphiphilic coat may be a polyethylene oxide-polypropylene oxide-polyethylene oxide triblock copolymer, a polyethylene oxide-polyglycoliclactic acid copolymer or a polyethylene oxide-polylactic acid copolymer.

Since the tumor-targeting gas-generating nanoparticle according to the present disclosure is accumulated in the tumor tissue in large quantity and generates strong ultrasound wave signals, it can be usefully used as a contrast agent for ultrasonic imaging. It exhibits superior performance for tumor-specific drug delivery owing to the enhanced permeation and retention effect, superior cell permeation, or the like.

BRIEF DESCRIPTION OF THE DRAWINGS

The above and other objects, features and advantages of the present disclosure will become apparent from the following description of certain exemplary embodiments given in conjunction with the accompanying drawings, in which.

3c compares fluorescence intensity from major organs and tumor after injection of a nanoparticle according to the present disclosure and a microparticle as a control

DETAILED DESCRIPTION OF EMBODIMENTS

Hereinafter, exemplary embodiments will be described in detail with reference to the accompanying drawings.

The present disclosure provides a tumor-targeting gas-generating nanoparticle (GGNP) that allows ultrasonic imaging and drug delivery at the same time. The GGNP according to the present disclosure includes a polycarbonate core that generates a gas and an amphiphilic coat. The GGNP according to the present disclosure has enhanced permeation and retention (EPR) effect and thus exhibits superior tumor-targeting performance.

Figure 1:
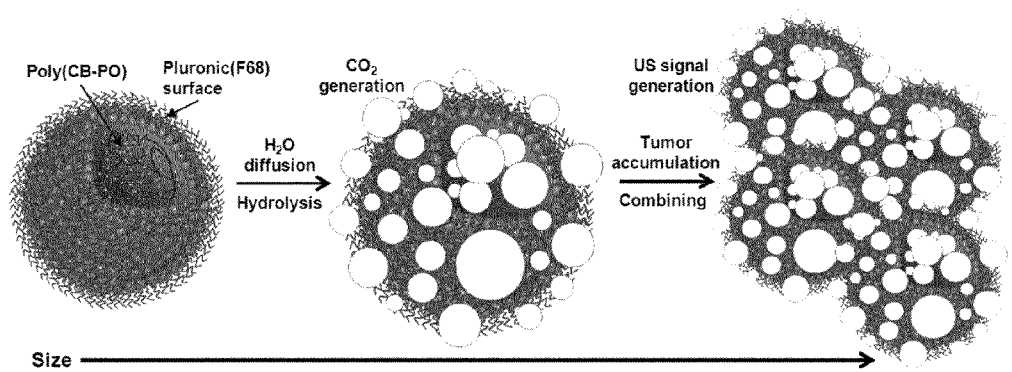
FIG. 1 schematically illustrates a mechanism by when a nanoparticle according to the present disclosure acts on a tumor tissue with time after being injected into the body.

When injected into the body, the GGNP according to the present disclosure becomes gradually larger in size with time as it generates a gas, aggregates with each other, is accumulated in large quantity in a tumor tissue and generates a strong ultrasound wave signal (see FIG. 1). As described in the Examples section, the inventors of the present disclosure observed change in size of the GGNP according to the present disclosure and in-vivo distribution thereof in a tumor-bearing mouse. After intravenously injecting the GGNP according to the present disclosure to a tumor-bearing mouse, generation of gas and intensity of ultrasound wave signals were evaluated under in-vitro condition and in-vivo condition. Also, its possibility for application to tumor-targeted drug delivery was tested in the same mouse model using docetaxel (DTX).

The GGNP according to the present disclosure may be prepared by synthesizing a polycarbonate core which is poly(cholesteryl γ-butyrolactone-b-propylene oxide) represented by Chemical Formula 1 and encapsulating the polycarbonate core with an amphiphilic coat:

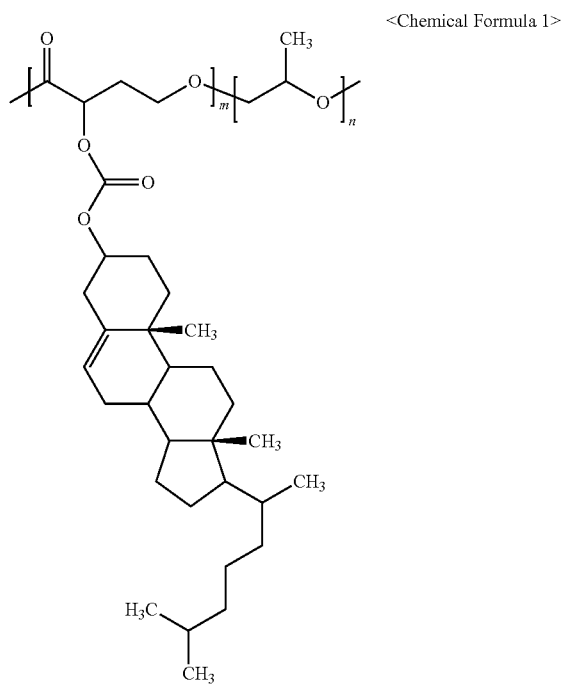

<Chemical Formula 1> wherein each of m and n is an integer from 1 to 1000.

The carbonate bond of the polycarbonate core may be broken by hydrolysis to produce a carbon dioxide bubble for generation of an ultrasound wave signal. The synthesized polymer may be encapsulated with an amphiphilic coat through oil-in-water (O/W) emulsification. The amphiphilic coat maintains the nanostructure of the GGNP according to the present disclosure and optimizes the rate of degradation of the polycarbonate core poly(CB-PO). In addition to a polyethylene oxide-polypropylene oxide-polyethylene oxide triblock copolymer (e.g., Pluronic F68 commercially available from BASF) described in the Examples section, various amphiphilic polymers such as a polyethylene oxide-polyglycoliclactic acid copolymer, a polyethylene oxide-polylactic acid copolymer, etc. may be widely used.

Figure 2A:
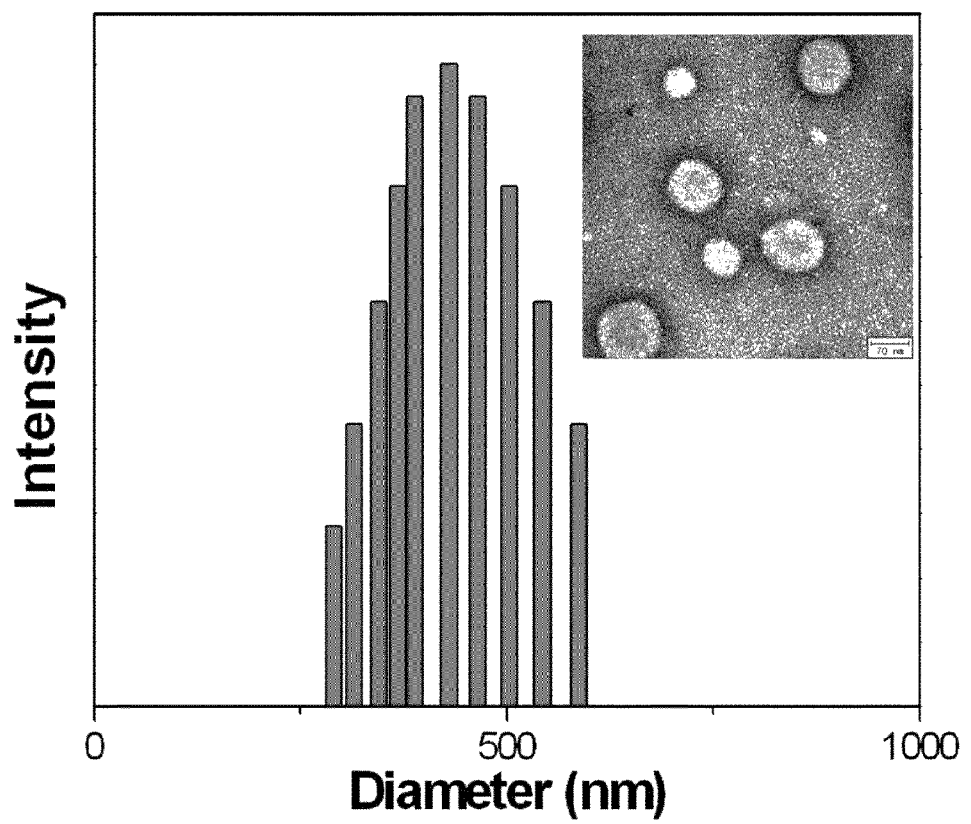
FIG. 2a shows a particle size distribution of a nanoparticle according to the present disclosure.
Figure 2B:
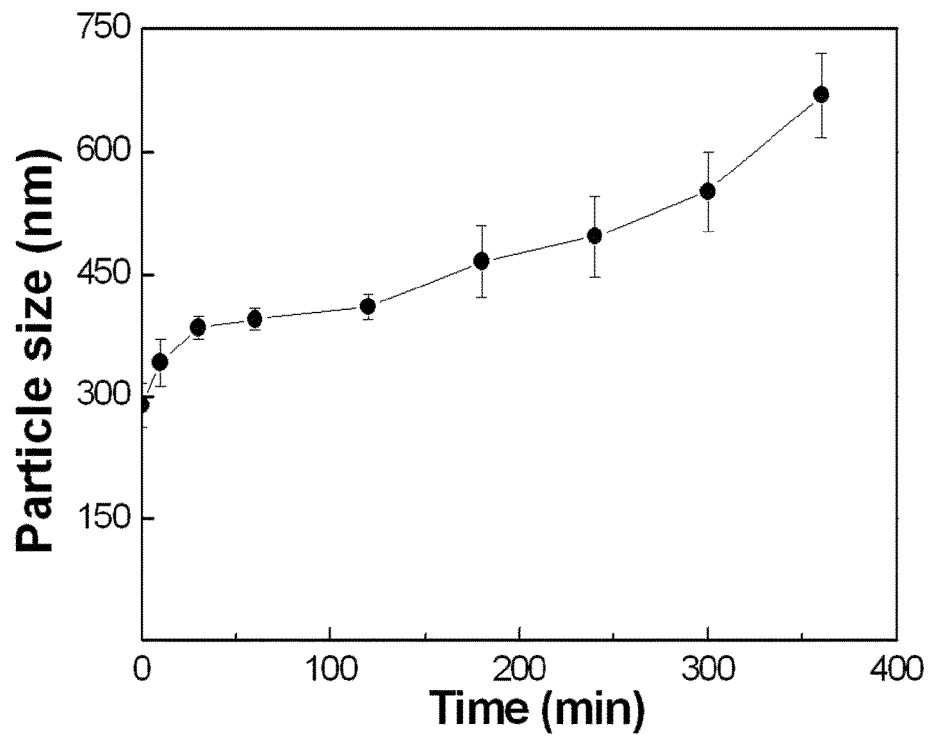
FIG. 2b shows change in particle size of a nanoparticle according to the present disclosure in an aqueous condition with time.
Figure 2C:
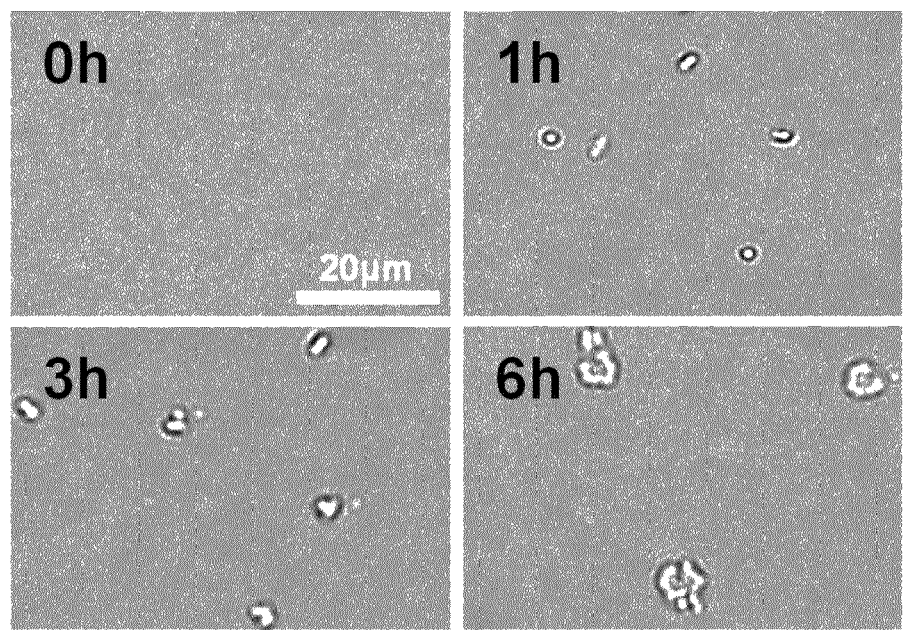
FIG. 2c shows microscopic images of a nanoparticle according to the present disclosure with time and FIG. 2d shows microscopic images showing that a nanoparticle according to the present disclosure grows into a flower shape with time.
Figure 2D:
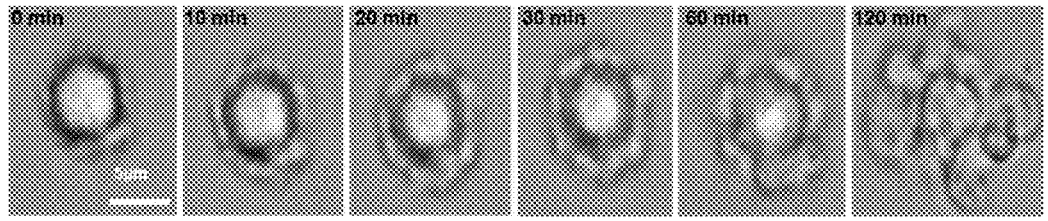

The GGNP according to the present disclosure has a spherical shape and a narrow particle size distribution of 300±50 nm (FIG. 2a). In an aqueous condition, the size of a single GGNP increases gradually due to the generation of a carbon dioxide gas (FIG. 2b). During this process, highly GGNPs dispersed with high concentration aggregate with each other and grow into a micrometer-scale aggregate that can be observed from a microscopic image (FIG. 2c). Although nanosized particles are not observed under a microscope, a considerable amount of micrometer-scale aggregates are observed 1 hour later and the size becomes larger 3-6 hours later. Generation of a gas from a micrometer-sized model particle (GGMP) whose composition is the same as that of GGNP is precisely observed with time under a microscope (FIG. 2d). With time, carbon dioxide gas is attached on the surface of the GGNP to result in a 'flower-shaped' structure.

Figure 3A:
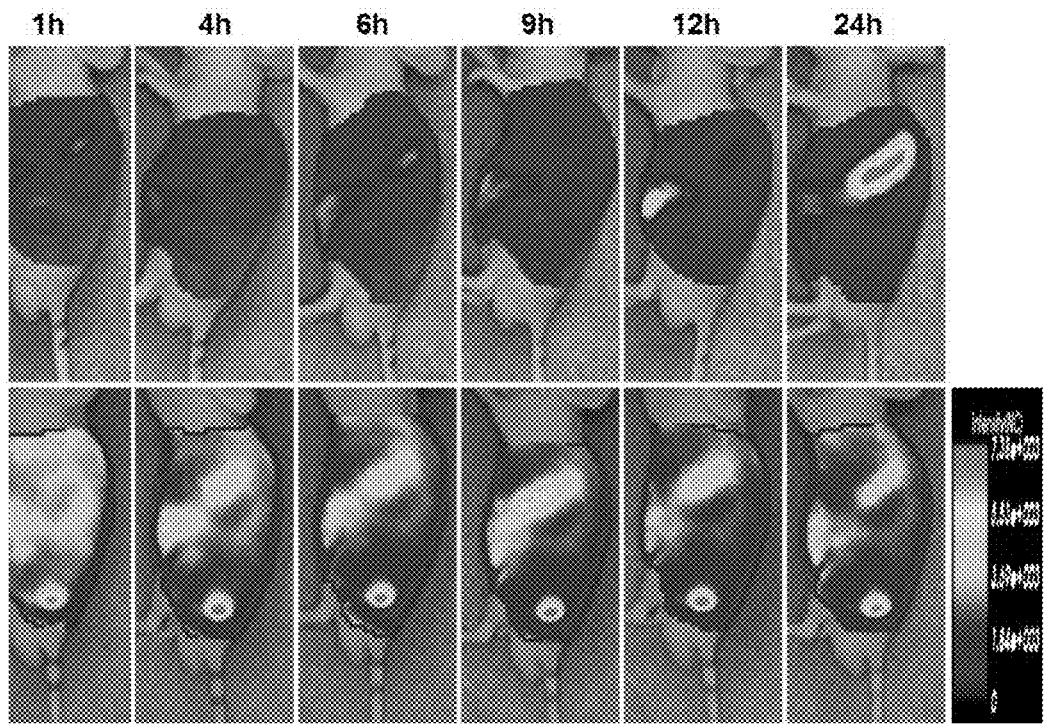
FIG. 3a shows an in-vivo distribution of a nanoparticle according to the present disclosure and a microparticle as a control with time after intravenous injection to a tumor-bearing mouse.
Figure 3B:
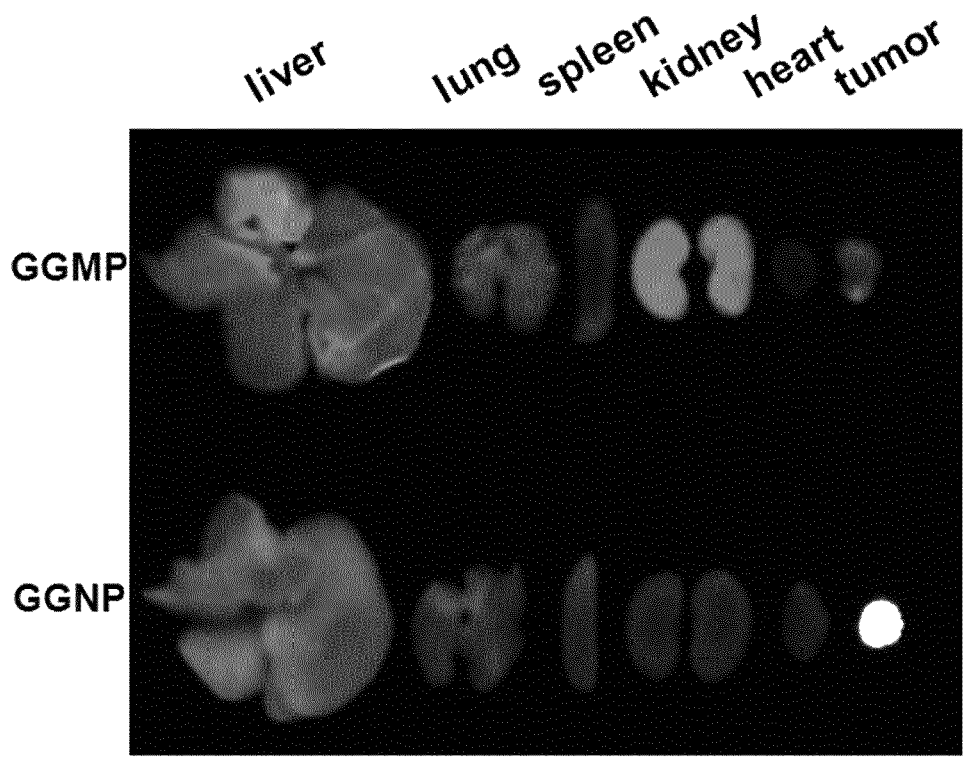
FIG. 3b shows an ex-vivo analysis result of major organs and tumor obtained by intravenously injecting a nanoparticle according to the present disclosure and a microparticle as a control and sacrificing the mouse 24 hours later, FIG.
Figure 3C:
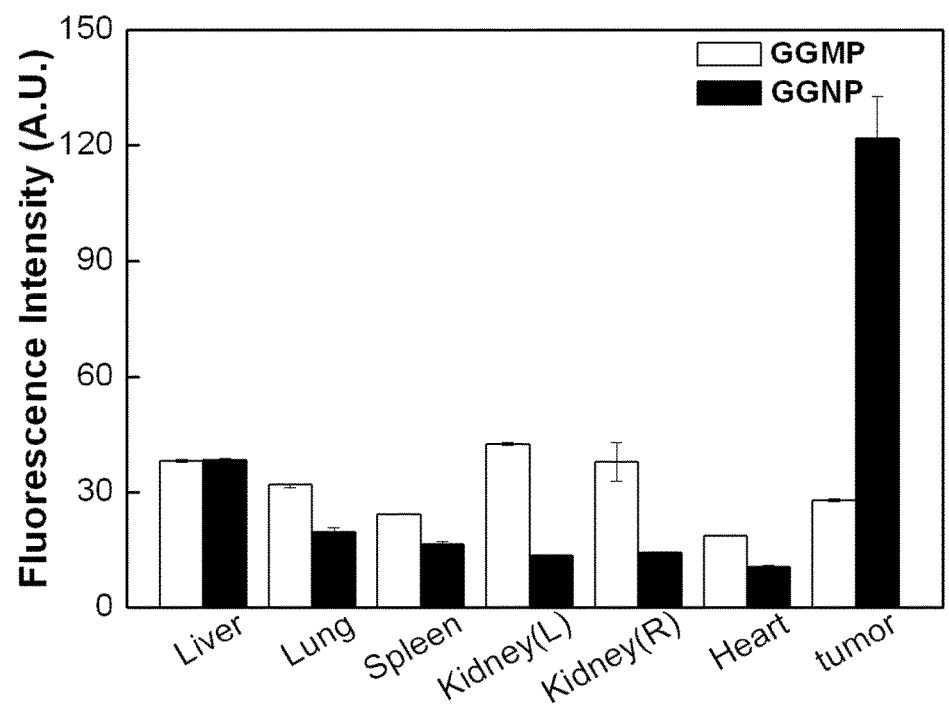
FIG. 3d shows fluorescence images of a tumor tissue after injection of a nanoparticle according to the present disclosure and a microparticle as a control.
Figure 3D:
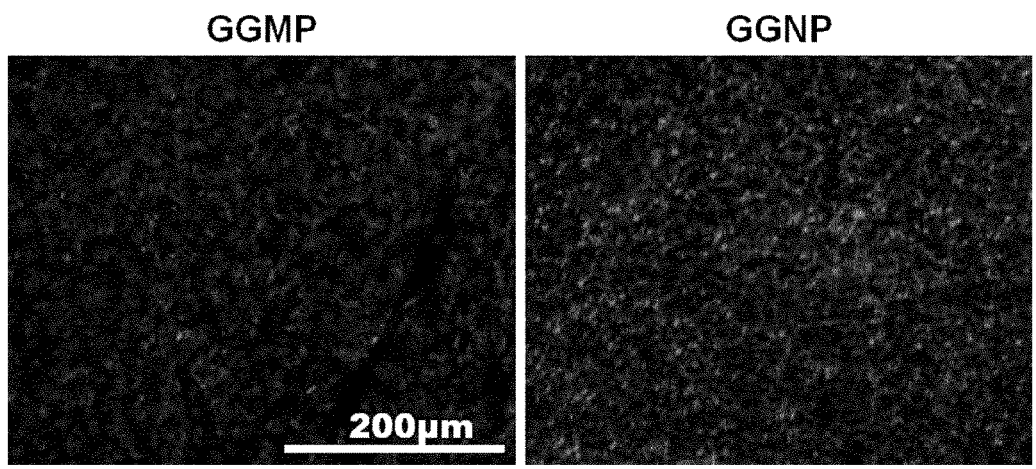

Since the GGNP according to the present disclosure has a nano size initially, it can circulate stably and be accumulated in a tumor with high concentration due to the EPR effect. In-vivo distribution of Cy5.5-labeled GGNP was evaluated after intravenous injection to a tumor-bearing mouse model (FIG. 3a). As expected, the GGMP as a control showed short circulation time and low accumulation in the tumor tissue. In contrast, the GGNP according to the present disclosure exhibited a strong fluorescence signal from the tumor tissue from 1 hour after the injection. The fluorescence intensity from the tumor reached maximum 12 hours later and the tumor tissue could be significantly distinguished from nearby tissues. The mouse was sacrificed 24 hours after the injection and major organs and tumor were analyzed ex vivo (FIG. 3b). The whole-body image revealed at least 3 times stronger fluorescence intensity from the tumor than from the other organs (FIG. 3c). However, the amount of the control GGMP in the tumor tissue was only about 23% of that of the GGNP according to the present disclosure and was accumulated mainly in the kidney due to short circulation time. From the fluorescence image of the tumor tissue, highly accumulated GGNPs were observed significantly in large quantity as strong red spots (FIG. 3d). These results demonstrate that, owing to the initial nano size and the EPR effect, the GGNP can be accumulated in the tumor tissue in large quantity after intravenous injection.

Figure 4A:
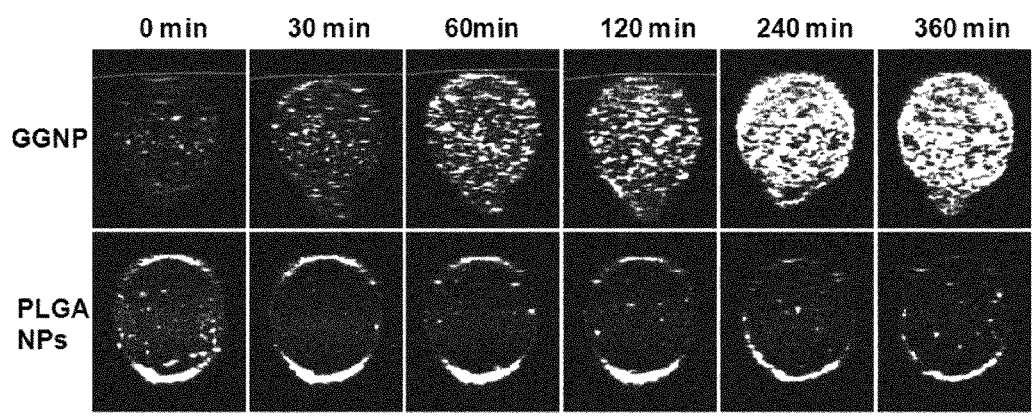
FIG. 4a shows ultrasonic images obtained by using a nanoparticle according to the present disclosure and a PLGA nanoparticle as a control as a contrast agent for ultrasonic imaging, FIG. 4b compares ultrasound intensity of a nanoparticle according to the present disclosure with a PLGA nanoparticle as a control with time.
Figure 4B:
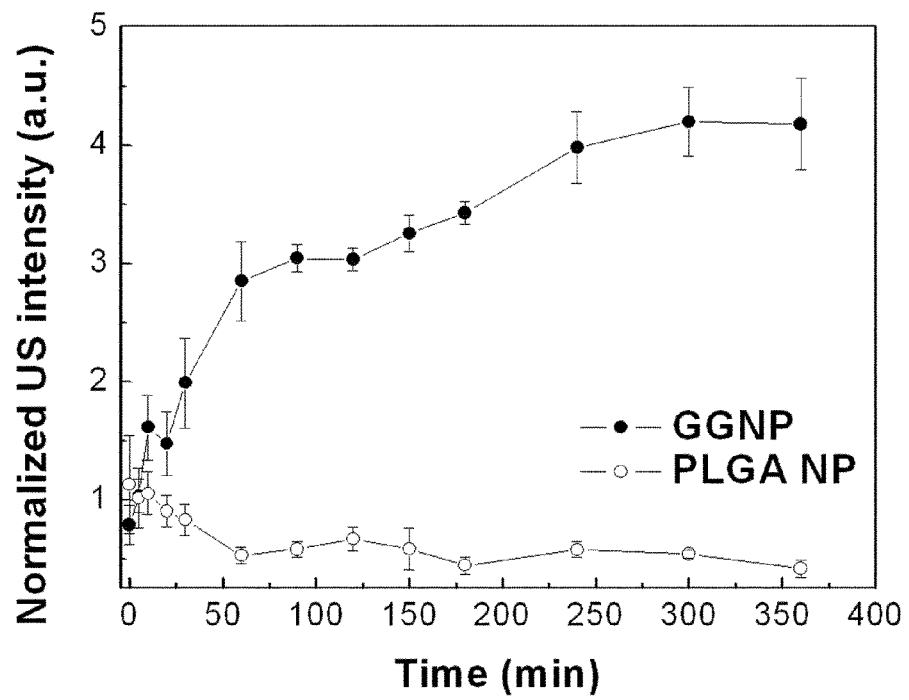
FIGS. 4c and 4d show a result of disrupting bubbles using a destructive mode high ultrasound and comparing ultrasound wave signals from a nanoparticle according to the present disclosure and Sono-Vue®, a commercially available contrast agent for ultrasonic imaging
FIGS. 4e and 4f show ultrasonic images and a graph obtained after intravenously injecting a nanoparticle according to the present disclosure to a tumor-bearing mouse model.
Figure 4C:
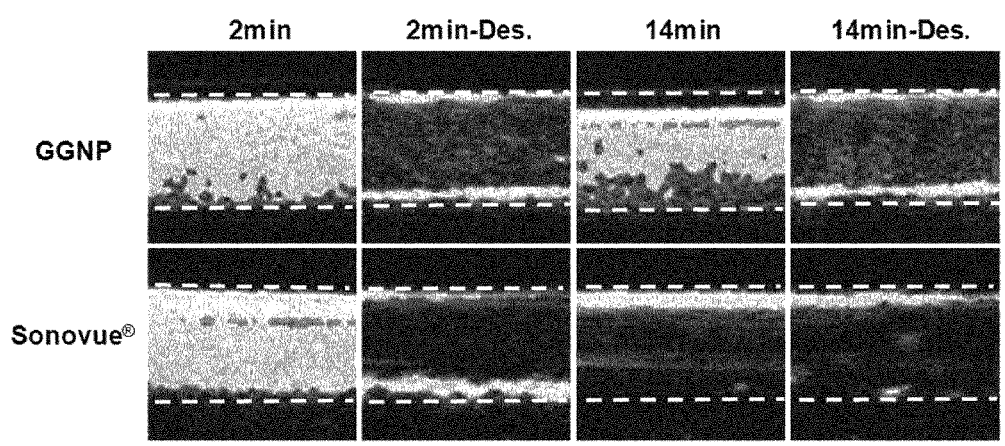
Figure 4D:
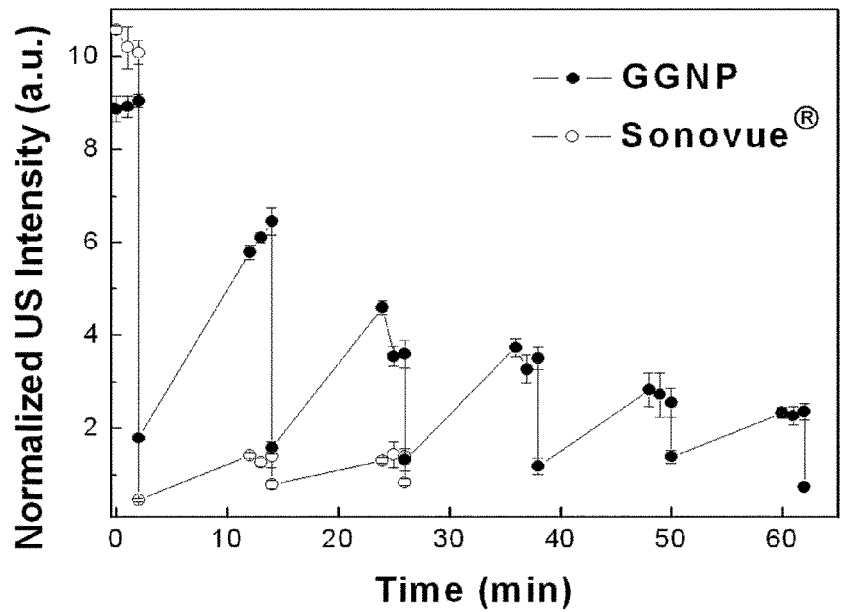
Figure 4E:
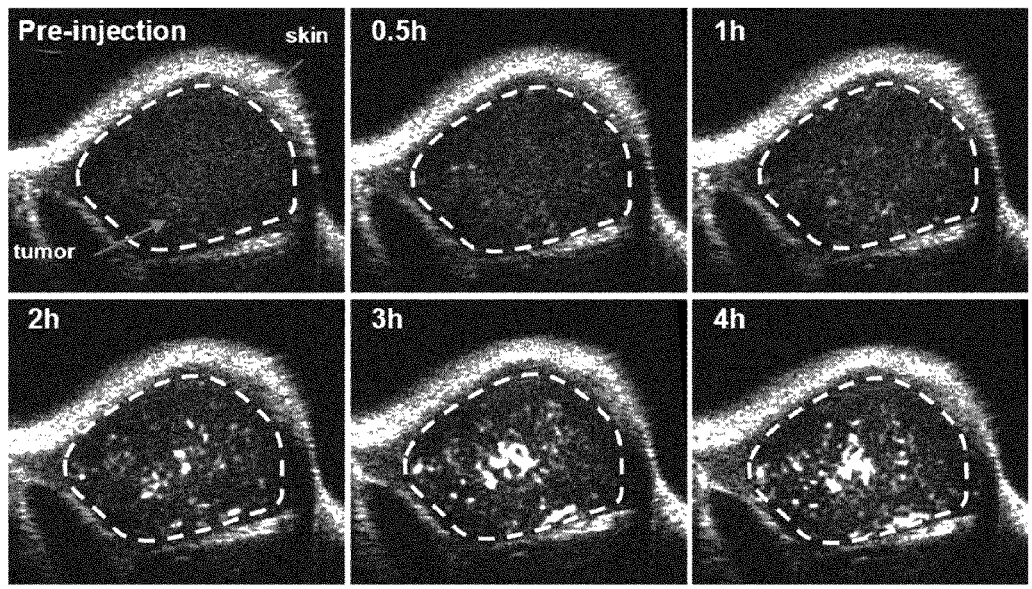
Figure 4F:
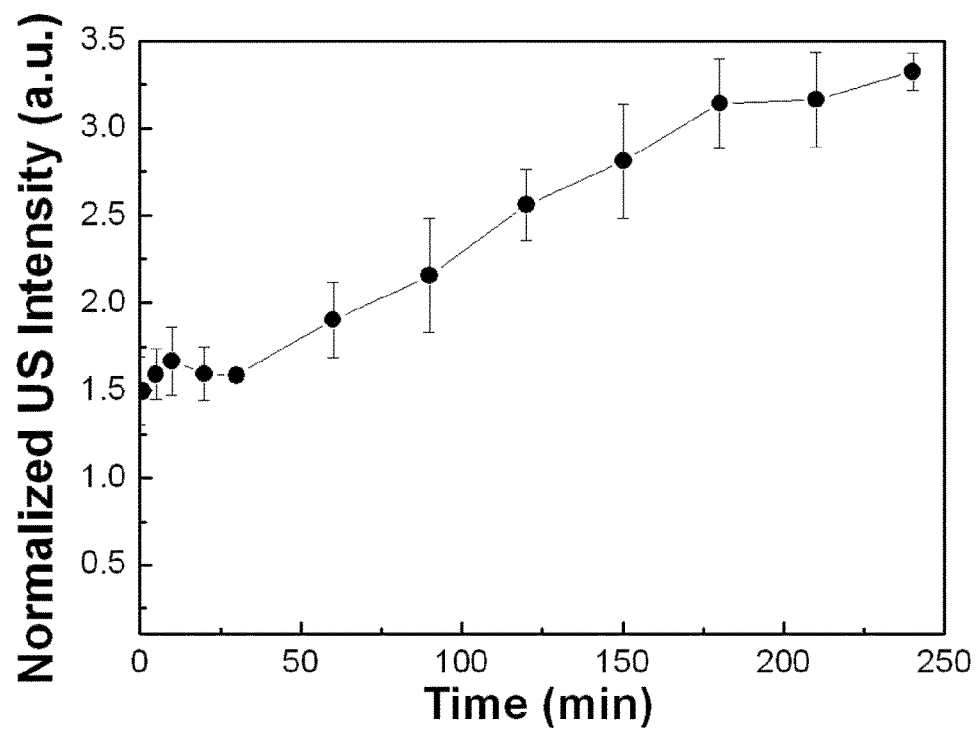

In order to evaluate the potential of as a contrast agent for ultrasonic imaging, ultrasound wave signals were obtained with time using an agar gel model. The in-vitro ultrasonic image of the GGNP according to the present disclosure showed no significant difference from the background initially, but the resolution was improved gradually with time (FIG. 4a). The control PLGA nanoparticle showed negligible change due to the lack of ability to generate gas. 5 hours later, the ultrasound intensity of the GGNP was about 8 times stronger than the initial value (FIG. 4b). Enhanced stability owing to continuous gas generation is another advantage of the GGNP according to the present disclosure in ultrasonic imaging as compared to the existing microbubble. When bubbles were disrupted using destructive mode high ultrasound, the ultrasound wave signals from the GGNP according to the present disclosure were restored 10 minutes later, whereas no restoration of ultrasound wave signal was observed for the commercially available contrast agent for ultrasonic imaging SonoVue® (FIGS. 4c and 4d). From the tumor of a tumor-bearing mouse model, ultrasound wave signals from the GGNP according to the present disclosure were observed with time. The ultrasonic image of the tumor became clear after the intravenous injection of the GGNP (FIG. 4e). At 4 hours after the injection, the intensity of the ultrasound wave signal from the tumor was increased to more than 2 times as compared to before the injection (FIG. 4f).

Figure 5A:
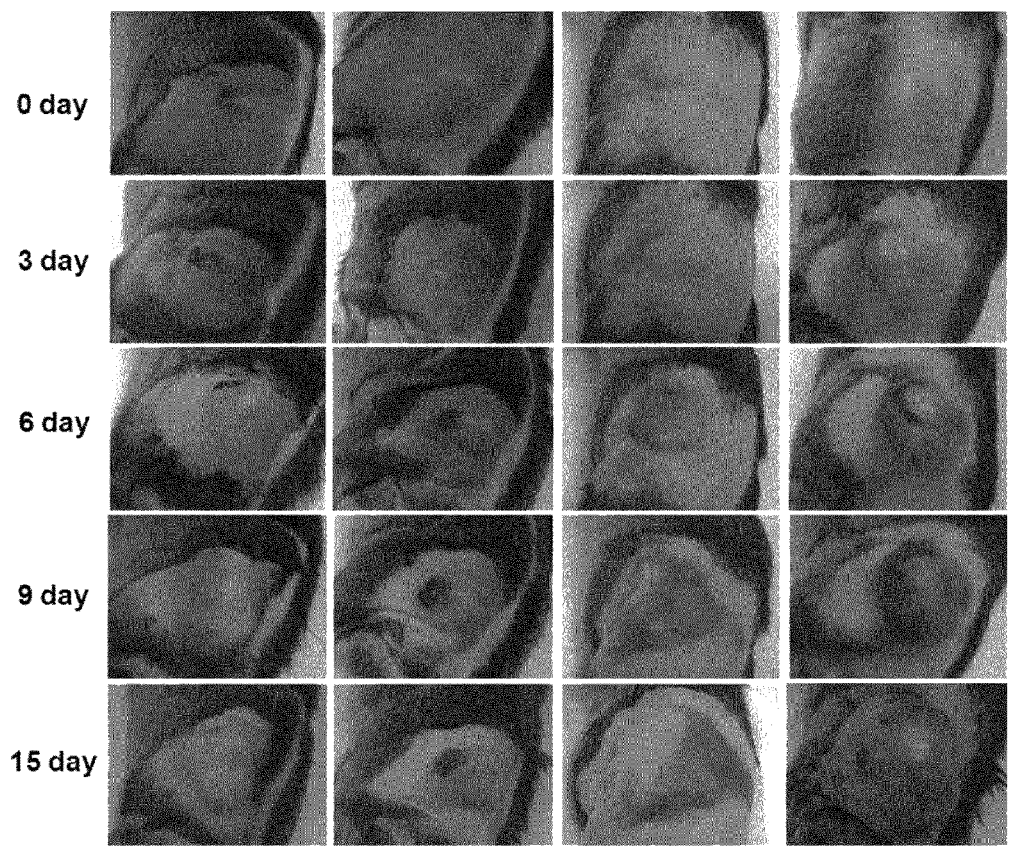
FIGS. 5a and 5b show photographs and a graph showing inhibition of tumor growth with time after treating a tumor-bearing mouse model with DTX-nanoparticle according to the present disclosure, DTX-nanoparticle according to the present disclosure+ultrasonication, free DTX or physiological saline, FIG. 5c compares the size of tumors extracted from each test group
Figure 5B:
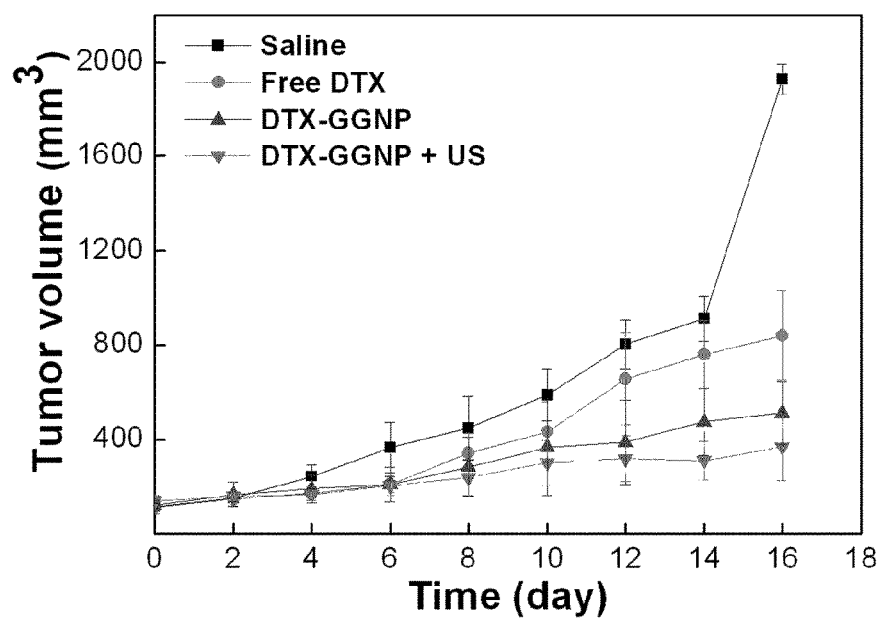
Figure 5C:
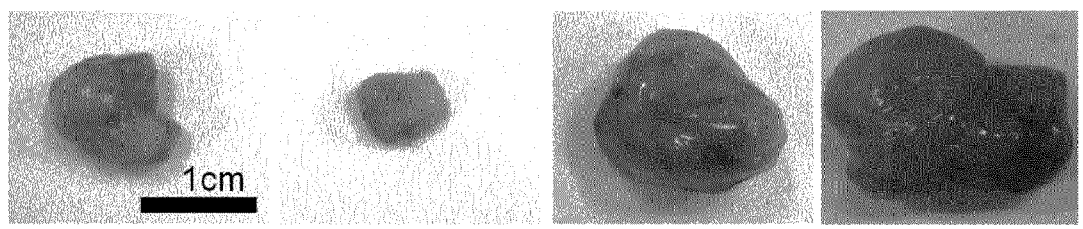
FIG. 5d shows images obtained through H&E and TUNEL staining for each test group.
Figure 5D:
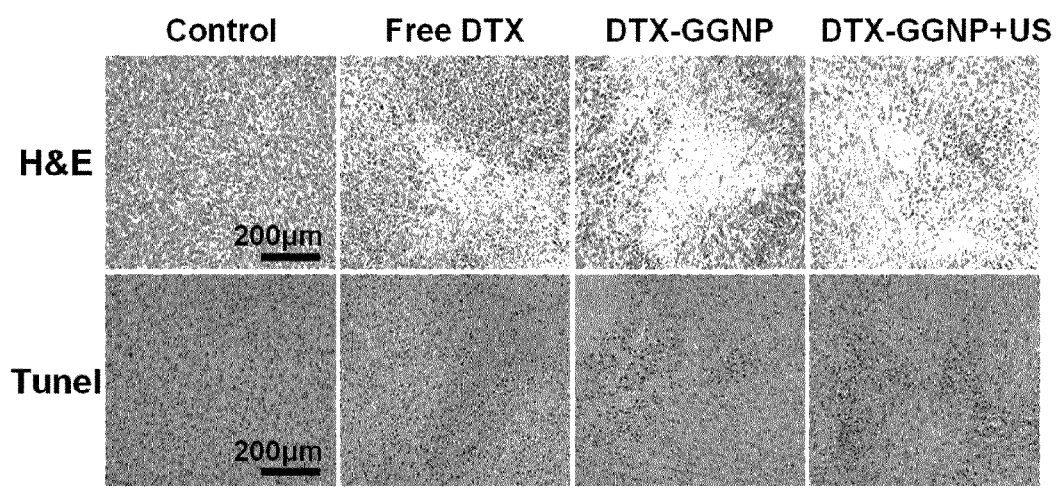

The tumor-targeted accumulation of the GGNP according to the present disclosure may be applied to drug delivery for treatment of tumor. When the GGNP according to the present disclosure is used for the purpose of drug delivery, a core including a hydrophobic anticancer drug DTX and a polycarbonate may be encapsulated with an amphiphilic coat to prepare a DTX-GGNP. As described in the Examples section, the loading efficiency and content of DTX in the GGNP according to the present disclosure were about 8.4% and 83.7%, respectively. When the DTX-GGNP was intravenously injected to a tumor-bearing mouse model, tumor growth was more successfully inhibited than when free DTX was injected (FIG. 5a). It is reported that disruption of a drug-loaded microbubble at the target site can improve permeation into blood vessel and cellular uptake of the drug through sonoporation (modification of permeability of the cell membrane using ultrasound). According to this report, the DTX-GGNP combined with bubble disruption provides more improved therapeutic effect than in the absence of the bubble disruption. In case of the DTX-GGNP according to the present disclosure, final tumor volume after 16 days was about 369 $mm^3$, which was 5.2 times smaller as compared to the groups treated with physiological saline or free DTX (FIG. 5b). Also, measurement of the size of the extracted tumor revealed that tumor growth was successfully inhibited by injection of the DTX-GGNP according to the present disclosure combined with bubble disruption (FIG. 5c). Histological analysis through H&E staining revealed that tumor tissue was damaged by the DTX-GGNP according to the present disclosure and TUNEL assay revealed apoptotic cells stained brown (FIG. 5d).

EXAMPLES

Hereinafter, the present disclosure will be described in more detail through examples. However, the following examples and experiments are for illustrative purposes only and not intended to limit the scope of this disclosure.

Example

Materials

Cholesteryl chloroformate, α-hydroxy-γ-butyrolactone, samarium, 1,2-diiodoethane, propylene oxide, Pluronic F68, tetrahydrofuran (THF), dichloromethane (DCM) and docetaxel were purchased from Sigma Chemical Co. (St. Louis, Mo., USA). THF was purified through 3 or more freeze-thawing cycles and dichloromethane was purified by distillation before use. SonoVue® was purchased from Bracco Diagnostics, Inc. (Milan, Italy).

Synthesis of Gas-Generating Polymer Poly(CB-PO)

A gas-generating polymer, poly(cholesteryl γ-butyrolactone-b-propylene oxide) (poly(CB-PO)), was synthesized through ring-opening polymerization of propylene oxide with cholesteryl-modified γ-butyrolactone. First, a cholesteryl-modified γ-butyrolactone monomer was prepared by substituting the hydroxyl group in the carbonate bond with cholesteryl chloroformate. Cholesteryl chloroformate (18 mmol, 8.08 g) and α-hydroxy-γ-butyrolactone (18 mmol, 1.83 g) were dissolved in DCM (50 mL) and pyridine (15 mL) was added dropwise to the resulting mixture solution in an ice bath under nitrogen atmosphere. 20 hours later, the mixture was washed with 1.0 M HCl and saturated $NaHCO_3$ and then washed 3 times with distilled water. After drying residual water with magnesium sulfate, the resulting solution was precipitated in a cold ethyl ether and dried in vacuum (yield=85.4%).

Ring-opening polymerization of the butyrolactone block copolymer was performed using samarium iodide/samarium ($SmI_2$/Sm) as an initiator, as described in the previous paper of the inventors of the present disclosure (Nanobubbles from Gas-Generating Polymeric Nanoparticles: Ultrasound Imaging of Living Subjects. *Angew. Chem. Int. Edit*. Volume 49, Issue 3, Pages 524-528. Published Online: 9 Dec. 2009). 1,2-Diiodoethane was washed with a sodium thiosulfate solution and, after drying residual water with $MgSO_4$, was dried for 24 hours in a vacuum oven. Distilled THF was slowly added to a mixture of the washed 1,2-diiodoethane (0.75 g, 5 mmol) and samarium powder (0.75 g, 5 mmol).

The cholesteryl-modified γ-butyrolactone and propylene oxide were polymerized under nitrogen atmosphere using the $SmI_2$/Sm initiator. During the reaction, the whole glass reactor was purged with vacuum and nitrogen. The cholesteryl-modified γ-butyrolactone (10 mmol, 5.15 g) was mixed with degassed toluene (10 mL) in a flask and propylene oxide (3.35 mmol, 0.195 g) was added while vigorously stirring. After raising temperature to 90° C., $SmI_2$/Sm (0.1 mmol, 1 mL) was added dropwise to the flask and the reaction mixture was kept at 90° C. for 48 hours under reduced pressure. Upon completion of the reaction, the solution was precipitated with ethyl ether and the resulting crude powder was dried in a vacuum oven (yield=68.2%).

Characterization of Poly(CB-PO)

Poly(CB-PO) was characterized by $^1$H nuclear magnetic resonance ($^1$H-NMR) analysis and Fourier transform infrared spectroscopy (FT-IR). $^1$H-NMR spectra were recorded at 300 MHz using the Varian Unity Plus 300 spectrometer. The sample was dissolved in $CDCl_3$ and tetramethylsilane (TMS) was used as internal standard. FT-IR spectra were recorded under nitrogen flow using the Perkin Elmer FT-IR system (Spectrum GX, MA, USA). The polymer sample was mixed with KBr powder and compressed into an IR window pellet. FT-IR spectra were measured at a resolution of 4 $cm^{-1}$ and 32 scans were accumulated for each spectrum.

Preparation of Gas-Generating Nanoparticle (GGNP)

A gas-generating nanoparticle (GGNP) consists of the poly (CB-PO) and Pluronic F68 and was prepared by O/W emulsification. To summarize, poly(CB-PO) dissolved in DCM (1 mL) containing 1.5% (w/w) Tween 80 and Pluronic F68 (10%, w/v), as oil phase, were dissolved in distilled water. Subsequently, the polymer solution was sonicated in an ice bath while adding a Pluronic F68 solution (5 mL) dropwise. The resulting nanoemulsion was transferred to a flask and dichloromethane was removed by magnetically stirring for 3 hours. The dried nanoemulsion was freeze-dried before use.

For drug delivery study, docetaxel (DTX) was used as an anticancer drug. In order to prepare DTX-loaded GGNP, DTX (10%, w/w) was dissolved in DCM containing the poly (CB-PO) added to a Pluronic F68 solution dropwise while sonicating. The resulting DTX-loaded nanoemulsion was stirred for 3 hours and then freeze-dried. The drug content and loading efficiency of the DTX-loaded nanoparticle was measured by high-performance liquid chromatography (HPLC; Agilent Tech. 1200 Series, CA, USA). Each sample solution was filtered through a 0.45-μm syringe filter and analyzed using Chemstation with an LC system using an XDB-C18 column (Agilent Tech., CA, USA). The mobile phase was acetonitrile/methanol (60:40) and flow rate was 1.2 mL/min. A calibration curve was drawn by plotting the DTX peak area against various DTX concentrations (0.1-100 μg/mL) monitored at 227 nm.

Characterization of GGNP

The particle size distribution of the GGNP was measured for 1 mg/mL nanoparticle emulsion in distilled water by dynamic light scattering (DLS; Spectra Physics, CA, USA). Measurement was made at 37° C. for 6 hours. The change in bubble size was monitored using a fluorescence microscope (BX51; Olympus Co. Ltd., Japan) equipped with a 40× focusing lens. 0.5 mg/mL nanoparticle or microparticle of the same composition was dispersed in PBS and temperature was kept at 37° C. throughout the measurement. Optical images were obtained by sampling one drop on the slide for 6 hours. The morphology of the GGNP was observed by transmission electron microscopy (TEM). The sample was prepared on a carbon-coated 400-mesh copper lattice and residual water was removed. After dropping a 5% (w/v) uranyl acetate solution, the sample solution was dried in the air. TEM images were obtained at 200 kV using CM-200 Philips (CA, USA).

In-Vitro Ultrasonic Imaging

Vevo 770® (high-resolution microimaging system; Visualsonics, Toronto, Canada) equipped with an RMV 706 converter was used to obtain in-vitro ultrasonic images at 40 MHz. A 3% (w/v) agar gel model was used as the in-vitro condition. The GGNP was dispersed in PBS (pH 7.4) at a concentration of 5 mg/mL. As a control, a PLGA nanoparticle was dispersed with the same concentration. The two samples were embedded in the agar gel model and ultrasonic images were obtained for 6 hours.

Gas generation from the GGNP was investigated by disrupting bubbles in the dispersion of the nanoparticle using high ultrasound. The GGNP and SonoVue® were dispersed at 10 mg/mL. The two samples were added to the agar gel model and ultrasonic images were obtained for 2 minutes. Then, high ultrasound was applied to each sample using the destructive mode of the Vevo 770® software. The samples were freely allowed to generate bubbles for 10 minutes. Ultrasonic images were obtained for 60 minutes with operation for 2 minutes and rest for 10 minutes. The normalized ultrasound intensity of the GGNP and SonoVue® was analyzed based on the difference in intensity of the space inside the model and the agar gel body.

In-vivo Ultrasonic Imaging

All experiments using living animals were conducted in compliance with the regulations and guidelines of the Korea Institute of Science and Technology (KIST) and approved by the institutional committee. 5.5-week-old C3H/HeN male mice were used in all animal studies except for fluorescence imaging (n=5 per group). For ultrasonic imaging, the mouse was anesthetized with isoflurane gas and hair was removed from the lower back. Then, $1 \times 10^6$ squamous cell carcinoma (SSC7) cells were subcutaneously injected into the lower back of the mouse. When the tumor was grown to a volume of 100-150 $mm^3$, 100 μL of a nanoparticle dispersion of 10 mg/mL GGNP was injected into the mouse via the tail vein. Then, the tumor was imaged for 4 hours by applying 40 MHz ultrasound using the Vevo 770® ultrasonic imaging system equipped with an RMV 706 probe (focal length: 6 mm). The contrast intensity of the ROI (tumor) of the ultrasonic image was calculated from considering the background (agar gel) attenuation.

In-vivo Fluorescence Imaging

For fluorescence imaging, the fluorescent dye Cy5.5-NHS was aminated with ethylenediamine, conjugated with Pluronic-NHS through amide bonding and then purified by dialysis. Subsequently, Cy5.5-labeled Pluronic 5 w/w % was bound to GGNP through O/W emulsification. Thus obtained Cy5.5-labeled GGNP and a microparticle as a control were dispersed in PBS (pH 7.4) and fluorescence intensity was normalized by US-V is spectroscopy (Lambda V is 7 spectrophotometer, Perkin-Elmer, CT). 5.5-week-old BALB/c male nude mice (n=4 per group) were used fluorescence imaged using the eXplore Optix system (Advanced Research Tech. Inc., Montreal, Canada). The BALB/c nude mouse tumor model was prepared using SCC7 cells in the same manner as the C3H/HeN mouse model. When the tumor was grown to a volume of 100-150 $mm^3$, 100 μL of a nanoparticle dispersion of 10 mg/mL GGNP was injected into the mouse via the tail vein. Then, fluorescence images were obtained for 24 hours by adjusting 40 μW laser power with 0.3-second points. For analysis of the biodistribution in organs, the mouse was sacrificed 24 hours later and internal organs were extracted and fixed in formaldehyde (4%, w/v) solutions. The fluorescence intensity of the nanoparticle from the organs was analyzed using a 12-bit CCD camera (Image Station 4000 mm; Kodak, New Haven, Conn.) equipped with a special C-mount lens and a Cy5.5 emission filter (600-700 nm; Omega Optical).

For fluorescence imaging, the tumor tissue of the mouse was embedded with Optimal Cutting Temperature (OCT) compound (Tissue-Tek®, CE, USA, CA) and fixed under an aqueous nitrogen condition. Each tumor tissue was cryosected to 6-μm thick slices and placed on a slide glass. Fluorescence images of the nanoparticle in the tumor tissue were obtained using a fluorescence microscope (1×81, Olympus, Japan) equipped with a Cy5.5 filter (Ex=673 nm, Em=692 nm).

In-vivo Tumor Treatment

The therapeutic effect of the DTX-loaded GGNP was evaluated using the same SCC-7 tumor-bearing C3H/HeN mouse model. The mice were divided into 4 treatment groups as follows: (1) physiological saline, (2) free DTX (10 mg/kg), (3) DTX-loaded GGNP (10 mg/kg DTX), (4) DTX-loaded GGNP (10 mg/kg DTX)+bubble disruption. When the tumor was grown to a volume of 100-150 mm$^3$, each solution was injected into the mouse via the tail vein once in 3 days. For bubble disruption, the destructive mode of the Vevo 770® ultrasonic imaging system was applied to the tumor site 3 hours after the injection of the nanoparticle. The tumor volume was recorded for 16 days with 2-day intervals. The tumor volume was calculated from a×b$^2$/2 (a and b are x-axis and y-axis lengths of the tumor). During the treatment, ultrasonic images of the tumor site were obtained before and after the injection of the solution. After the treatment, the mouse was sacrificed and the tumor was extracted, fixed with paraffin and prepared into 10-µm slices. The images of the tumor tissue were obtained using a fluorescence microscope (BX51) equipped with a ×20 focusing lens.

In-vitro Cytotoxicity Test

The cytotoxicity of the GGNP was evaluated by the 3-(4, 5-dimethylthiazol-2-yl)-2,5-diphenyltetrazolim bromide (MTT) assay. SCC7 cells were cultured in RPMI1640 containing antibiotics (1%) and fetal bovine serum (10%). The SCC7 cells were seeded onto a 96-well tissue culture plate with 1×10$^4$ cells per well and incubated at 37° C. for 24 hours under carbon dioxide atmosphere. After washing the SCC7 cells with PBS, the GGNP was diluted with the cell culture medium (1 µg to 10 mg/mL) and 200 µL of the sample was added to the cells dropwise. After further incubating for 2 hours in a fresh medium containing MTT, absorbance was measured at 570 nm using a microplate reader (VERSA-max™, Molecular Devices Corp., Sunnyvale, Calif.) and cell viability was calculated.

Evaluation

The well-known key features of the nanoparticle for in-vivo tumor targeting are optimized size suitable for the EPR effect and surface characteristics. Since the biodistribution of the nanoparticle is determined within a few hours after the intravenous injection, it is necessary to optimize the size and surface characteristics of the GGNP for in-vivo tumor targeting. Because the change in size and aggregation of the GGNP are dependent on the hydrolysis of the carbonate bond, the inventors of the present disclosure tried to control the contact of the poly(CB-PO) with water by means of a stable Pluronic F68 coat. This optimized structure allows stable circulation and accumulation in the tumor at high concentration through continuous carbon dioxide gas generation. In addition, the hydrophilic polyethylene glycol group of Pluronic F68 may prevent aggregation of the nanoparticle with serum proteins. After the nanoparticle is accumulated in the tumor site in large quantity, the gas generated from the particle surface covers the Pluronic F68 coat. As a result, the particles may aggregate to grow into a microbubble and may generate strong ultrasound wave signals from the tumor tissue.

Another advantage of the GGNP according to the present disclosure over the existing microbubble is that ultrasound wave signals can be generated stably in in-vivo condition for a long time. In general, the half-life of the injected microbubble in the blood is only a few minutes. The contiguous gas-generating system based on nano size can overcome this problem and allows in-vivo ultrasonic imaging for a long time. As demonstrated from the bubble disruption test, even when bubbles are disrupted due to repeated ultrasonic imaging or external force such as collision to the blood vessel wall, the newly generated GGNP bubbles ensure strong ultrasound wave signals.

The tumor-targeted delivery of the GGNP according to the present disclosure may be utilized for other types of imaging or drug delivery. In this case, other contrast agents or drugs will be included in the GGNP. According to experiments conducted by the inventors of the present disclosure, the anticancer drug DTX and iron oxide nanoparticle were successfully encapsulated in the GGNP and delivered to the tumor tissue at the same time. The amphiphilic structure of the GGNP based on the Pluronic F68 polymer is also suitable for transporting other hydrophobic molecules in addition to the poly(CB-PO). Further, the terminal group of Pluronic F68 may be further modified with other molecule such as Cy5.5 for optical imaging. The improved therapeutic effect and advanced MR images obtained for the tumor-bearing mouse model demonstrate that the GGNP according to the present disclosure can be applied to various types of imaging and theragnosis.

For biomedical use, the nanoparticle should be nontoxic and biocompatible. The GGNP according to the present disclosure mainly consists of poly(CB-PO) and Pluronic F68. The poly(CB-PO) has two degradable bonds, i.e. the carbonate bond and the ester bond. The carbonate bond can be easily degraded by hydrolysis upon contact with water and the ester bond is also known to be degradable within a few days in the body. After the degradation of the two bonds, cholesterol and polypropylene glycol oligomers are produced. These molecules are biocompatible and small enough to be excreted out of the body. Pluronic F68 is also a biocompatible substance and clinical use is approved by the FDA. Further, the cell viability data obtained from the MTT assay support the superior biocompatibility of the GGNP according to the present disclosure. Accordingly, the GGNP according to the present disclosure is expected to have no problem for biomedical use.

To summarize, the present disclosure provides the tumor-targeting GGNP for in-vivo ultrasonic imaging, MR imaging and drug delivery. The GGNP according to the present disclosure includes a gas-generating poly(CB-PO) having a carbonate bond and a Pluronic F68 coat and its structure is reasonably optimized for time-dependent gas generation and ultrasonic imaging. After intravenous injection, the GGNP according to the present disclosure can be accumulated in the tumor tissue in large quantity through the EPR effect owing to the nano size. Then, the generated carbon dioxide gas covers the surface of the GGNP and the GGNPs aggregate with each other to generate strong ultrasound wave signals in the tumor tissue. In addition, since the GGNP according to the present disclosure can be accumulated in the tumor tissue in large quantity, it can be used for drug delivery and MR imaging. Accordingly, the GGNP according to the present disclosure has a considerable potential not only as a contrast agent for ultrasonic imaging but also as a tumor-targeting platform for various types of imaging and theragnosis.

While the present disclosure has been described with respect to the specific embodiments, it will be apparent to those skilled in the art that various changes and modifications may be made without departing from the spirit and scope of the disclosure as defined in the following claims.

What is claimed is:

1. A tumor-targeting gas-generating nanoparticle comprising a polycarbonate core and an amphiphilic coat, the amphiphilic coat being a polyethylene oxide-polypropylene oxide-polyethylene oxide triblock copolymer, a polyethylene oxide-polyglycoliclactic acid copolymer or a polyethylene oxide-polylactic acid copolymer, wherein the polycarbonate core is poly(cholesteryl γ-butyrolactone-b-propylene oxide) represented by Chemical Formula 1:

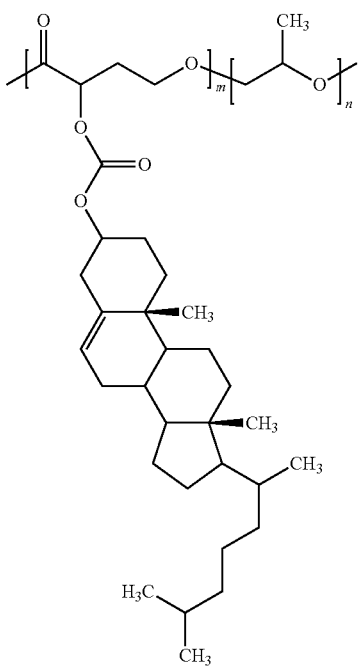

wherein each of m and n is an integer from 1 to 1000.

2. The tumor-targeting gas-generating nanoparticle according to claim 1, wherein the amphiphilic coat is a polyethylene oxide-polypropylene oxide-polyethylene oxide triblock copolymer.

3. The tumor-targeting gas-generating nanoparticle according to claim 1, wherein the nanoparticle has a particle size distribution of 300±50 nm.

4. A method for preparing a tumor-targeting gas-generating nanoparticle, comprising:
synthesizing a polycarbonate core through ring-opening polymerization, wherein the polycarbonate core is poly(cholesteryl γ-butyrolactone-b-propylene oxide) represented by Chemical Formula 1:

<Chemical Formula 1>

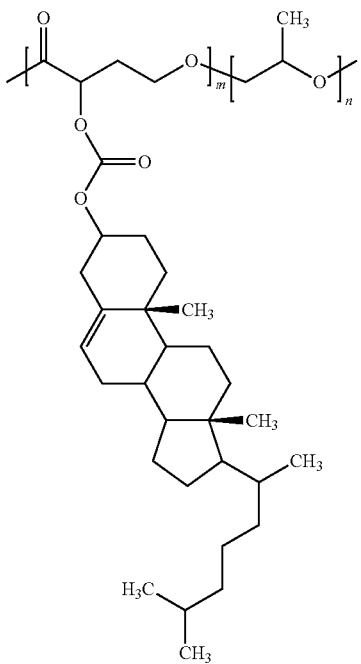

wherein each of m and n is an integer from 1 to 1000; and in its place
encapsulating the polycarbonate core with an amphiphilic coat through oil-in-water emulsification, the amphiphilic coat being a polyethylene oxide-polypropylene oxide-polyethylene oxide triblock copolymer, a polyethylene oxide-polyglycoliclactic acid copolymer or a polyethylene oxide-polylactic acid copolymer.

5. The method for preparing a tumor-targeting gas-generating nanoparticle according to claim 4, wherein the amphiphilic coat is a polyethylene oxide-polypropylene oxide-polyethylene oxide triblock copolymer.

6. A tumor-targeting nanoparticle for drug delivery comprising:
a core comprising a drug to be delivered and a polycarbonate; and
an amphiphilic coat that is a polyethylene oxide-polypropylene oxide-polyethylene oxide triblock copolymer, a polyethylene oxide-polyglycoliclactic acid copolymer or a polyethylene oxide-polylactic acid copolymer,
wherein the polycarbonate core is poly(cholestervi y-butyrolactone-b-propylene oxide) represented b Chemical Formula 1:

<Chemical Formula 1>

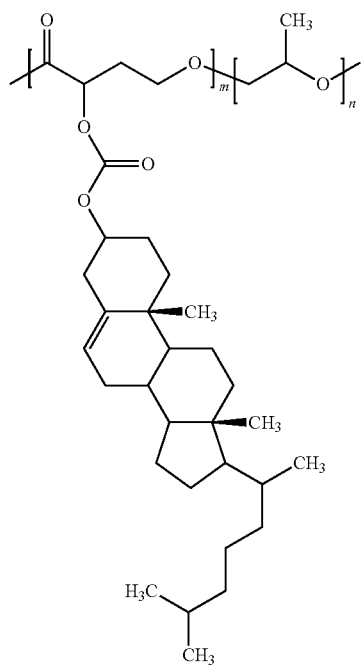

wherein each of m and n is an integer from 1 to 1000.

7. The tumor-targeting nanoparticle for drug delivery according to claim 6, wherein the amphiphilic coat is a polyethylene oxide-polypropylene oxide-polyethylene oxide triblock copolymer.

* * * * *